(12) United States Patent
Pandey et al.

(10) Patent No.: US 6,791,009 B1
(45) Date of Patent: Sep. 14, 2004

(54) TRANSGENIC PLANTS WITH ENHANCED CHLOROPHYLL CONTENT AND SALT TOLERANCE

(75) Inventors: Girdhar Kumar Pandey, New Delhi (IN); Vanga Siva Reddy, New Delhi (IN); Renu Deswal, New Delhi (IN); Alok Bhattacharya, New Delhi (IN); Sudhir Kumar Sopory, New Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/503,191

(22) Filed: Feb. 14, 2000

(51) Int. Cl.$^7$ .............................. C12N 15/82; A01H 5/00
(52) U.S. Cl. ....................... 800/282; 800/286; 800/298; 435/320.1
(58) Field of Search .............................. 435/320.1, 419, 435/468; 800/286, 282, 298

(56) References Cited

PUBLICATIONS

Cockcroft et al, Cyclin D control of growth rate in plants, Jun. 2000, Nature vol. 405 pp. 575–579.*
Riou–Khamlichi et al, Cytokinin Activation of Arabidopsis Cell Division Through a D–Type Cyclin, Mar. 1999, Science vol. 283 pp. 1541–1544.*
Nagendra Yadava et al., "Characterization of EhCaBP, a calcium–binding protein of *Entamoeba histolytica* and its binding proteins", Molecular and Biochemical Parasitology 84 (1997) 69–82.
Jayendra Prasad et al., "The Calcium Binding Protein of *Entamoeba histolytica*: Expression in *Escherichia coli* and Immunochemical Characterization", Cellular and Molecular Biology Research, vol. 39, pp 167–175, 1993.
Jayendra Prasad et al., Short Communication, "Cloning and sequence analysis of a calcium–binding protein gene from a pathogenic strain of *Entamoeba histolytica*", Molecular and Biochemical Parasitology 52 (1992) 137–140.
B. W. Poovaiah et al. "Regulated Expression of a Calmodulin Isoform Alters Growth and Development in Potato" *Journal of Plant Physiology*, vol. 149, pp. 553–558 (1996).
Raymond E. Zielinski et al. "Structure And Expression of Genes Encoding Calcium–Modulated Proteins In Higher Plants" *Current Topics in Plant Biochemistry and Physiology*, vol. 9, pp. 141–152 (1990).

* cited by examiner

*Primary Examiner*—Elizabeth F. McElwain
*Assistant Examiner*—Cynthia Collins
(74) *Attorney, Agent, or Firm*—Nixon Peabody LLP; Donald R. Studebaker

(57) ABSTRACT

The present invention relates to novel nucleic acid construct comprising (a) an anti-sense gene of a sense gene encoding *E. histolytica* calcium binding protein or a portion of said anti-sense gene, wherein said sense gene is at least 90% similar to the nucleic sequence of SEQ ID No: 1, and wherein said portion of the anti-sense gene is of a size capable of disrupting translation of said calcium binding protein; and (b) a constitutive promoter and a nopaline synthase (nos) polyadenylation signal sequence both operatively linked to said gene or portion thereof; wherein said construct is useful for increasing the level of chlorophyll in plants, a transgenic plant containing said construct and a novel nucleic acid construct useful for developing stress-tolerant plants, comprising (a) a sense gene encoding *E. histolytica* calcium binding or an altered sense gene wherein said gene encodes proteins of a sequence having biological properties identical to the said sense gene, and (b) the constitutive promoter and the nopaline synthase (nos) polyadenylation signal sequence both operatively linked to said gene or portion thereof.

5 Claims, 4 Drawing Sheets

Figure 2:
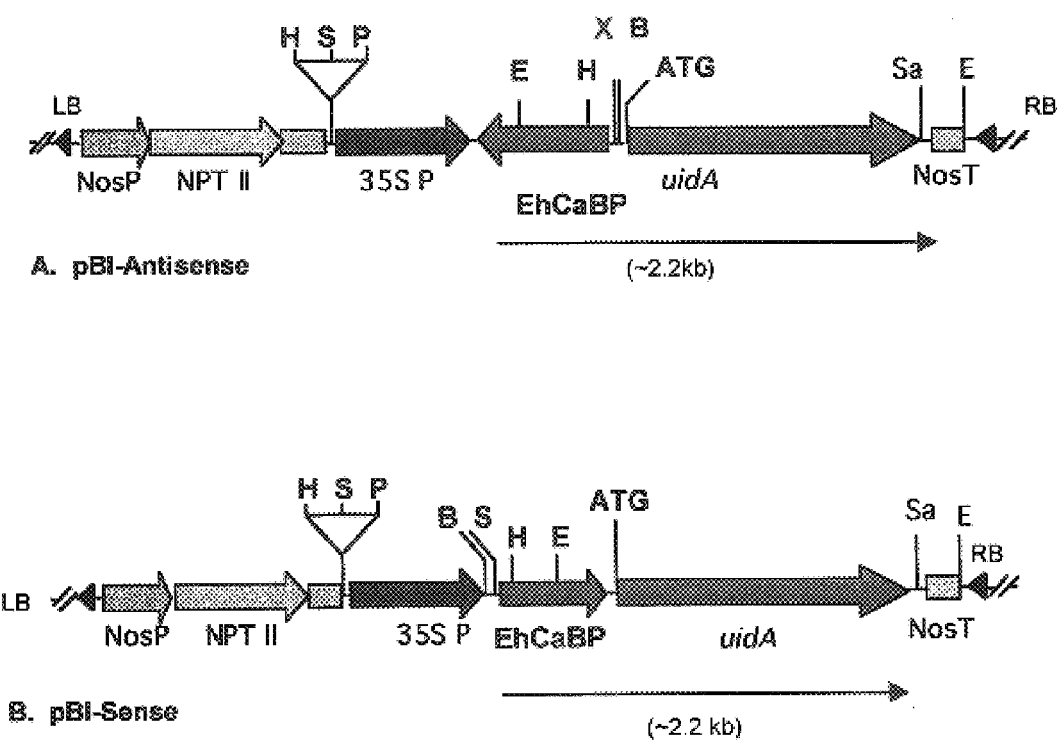

(2 of 4 Drawing Sheet(s) Filed in Color)

FIG. 1

SEQUENCE LISTING
(1) GENERAL INFORMATION:
(iii) NUMBER OF SEQUENCES:2
(2) INFORMATION FOR SEQ ID NO.: 1:
(i) SEQUENCE CHARACTERISTICS:
(A) LENGTH : 405 base pairs
(B) TYPE: nucleic acid
(C) STRANDEDNESS: double
(D) TOPOLOGY: linear
(ix) FEATURE:
(A) NAME/KEY: CDS
(B) LOCATION: 1...405
(xi)SEQUENCE DESCRIPTION: SEQ ID NO: 1:
ATG GCT GAA GCA CTT TTT AAA GAA ATT GAT GTT AAT GGA GAT GGA GCT GTC TCT TAT GAA 60
Met Ala Glu Ala Leu Phe Lys Glu Ile Asp Val Asn Gly Asp Gly Ala Val Ser Tyr Glu GAA GTT AAA GCT TTT GTT TCA AAG AAG AGA GCA ATT AAG AAT GAA CAA CTT CTT CAA TTA 120
Glu Val Lys Ala Phe Val Ser Lys Lys Arg Ala Ile Lys Asn Glu Gln Leu Leu Gln Leu ATT TTC AAA TCT ATT GAT GCT GAT GGA AAT GGA GAA AAT GAT CAA AAT GAA TTT GCT AAA 180
Ile Phe Lys Ser Ile Asp Ala Asp Gly Asn Gly Glu Asn Asp Gln Asn Glu Phe Ala Lys TTC TAT GGA TCA ATT CAA GGA CAA GAT CTT TCT GAT GAT AAG ATT GAA TTG AAA GTA CTC 240
Phe Tyr Gly Ser Ile Gln Gly Gln Asp Leu Ser Asp Asp Lys Ile Glu Leu Lys Val Leu TAT AAA CTT ATG GAT GTT GAT GGA GAT GGA AAA TTA ACT AAA GAA GAA GTT ACT TCA TTC 300
Tyr Lys Leu Met Asp Val Asp Gly Asp Gly Lys Leu Thr Lys Glu Glu Val Thr Ser Phe TTT AAA AAG CAT GGT ATT GAA AAG GTT GCT GAA CAA GTT ATG AAA GCT GAT GCT AAT GGT 360
Phe Lys Lys His Gly Ile Glu Lys Val Ala Glu Gln Val Met Lys Ala Asp Ala Asn Gly GAT GGA TAT ATC ACA CTT GAA GAA TTC CTT GAG TTT TCA CTC TAA 405
Asp Gly Tyr Ile Thr Leu Glu Glu Phe Leu Glu Phe Ser Leu *

(2) INFORMATION FOR SEQ ID NO.: 2:
(i) SEQUENCE CHARACTERISTICS:
(A) LENGTH : 134 amino acids
(B) TYPE: amino acid
(C) TOPOLOGY: linear
(ii) MOLECULE TYPE: protein
(xi) SEQUENCE DESCRIPTION: SEQ ID NO: 2:
Met Ala Glu Ala Leu Phe Lys Glu Ile Asp Val Asn Gly Asp Gly Ala Val Ser Tyr Glu

FIG. 1(cont'd)

Glu Val Lys Ala Phe Val Ser Lys Lys Arg Ala Ile Lys Asn Glu Gln Leu Leu Gln Leu

Ile Phe Lys Ser Ile Asp Ala Asp Gly Asn Gly Glu Asn Asp Gln Asn Glu Phe Ala Lys

Phe Tyr Gly Ser Ile Gln Gly Gln Asp Leu Ser Asp Asp Lys Ile Glu Leu Lys Val Leu

Tyr Lys Leu Met Asp Val Asp Gly Asp Gly Lys Leu Thr Lys Glu Glu Val Thr Ser Phe

Phe Lys Lys His Gly Ile Glu Lys Val Ala Glu Gln Val Met Lys Ala Asp Ala Asn Gly

Asp Gly Tyr Ile Thr Leu Glu Glu Phe Leu Glu Phe Ser Leu

TRANSGENIC PLANTS WITH ENHANCED CHLOROPHYLL CONTENT AND SALT TOLERANCE

FIELD

The present invention relates to application of recombinant DNA technology to plants. More specifically, the invention relates to the development of transgenic plants with enhanced chlorophyll content and enhanced salt tolerance.

BACKGROUND

Calcium plays an important role in cellular regulation in almost all organisms. Reference can be made to (Bootman, M D and Berridge, M J, 1995, The elemental principles of calcium signaling, Cell, 83, 675–678.) wherein the authors have described the importance of calcium signaling that acts as a secondary messenger through a series of calcium binding proteins. These proteins bind calcium and subsequently either directly or indirectly through another set of proteins, carry out different biological functions. Reference can be made to (Roberts, D M and Harmon, A C, 1992, Calcium modulated proteins: targets of intracellular calcium signals in higher plants, Ann. Rev. Plant Physiol. Plant Mol. Biology, 43, 375–414) wherein the authors have described various calcium modulated proteins including the calcium stimulated kinases and their involvement in various biological functions in plants. Calcium binding domains of many of these proteins have been characterized. Different calcium binding proteins have different number of calcium binding domains. Reference can be made to (Jang, H J, Pih, K T, Kang, S G, Lim, J H, Jim, J B, Piao, H L and Hwang, I, 1998, Molecular cloning of a novel calcium binding protein that is induced by NaCl stress, Plant Molecular Biology, 37, 839–847.) wherein the authors have described a novel salt stress induced calcium binding protein having three calcium binding loops as compared to 4 domains present in calmodulin. Though many calcium binding proteins have been reported in the literature, there are still a host of other proteins that have not yet been reported. Besides the biological role of many of these calcium binding proteins is not clear. Since calcium plays such an important role in biological systems it is important to characterise novel calcium binding proteins and decipher their role. A novel calcium binding protein from the protozoan parasite *Entamoeba histolytica* has recently been described by one of the applicants and regarding this, reference can be made to Prasad, J, Bhattacharya, S Bhattacharya, A, 1992, (Cloning and sequence analysis of a calcium binding protein gene from a pathogenic strain of *Entamoeba histolytica*. Mol. Biochem. Parasitol. 52, 137–140.), wherein the authors have described the properties of this novel EhCaBP and shown how this protein is different from well characterized calcium binding protein (CaBP), calmodulin. Nucleotide sequence comparison with the existing databases showed that it is a new kind of calcium binding protein not described so far.

Further, Prasad et al in Cellular and Molecular Biology Research, Vol. 39, pp.167–175, 1993 reported the expression of the EhCaBP in *E.coli*. and the use thereof to generate polyclonal antibodies. Nagendra Yadava et al in Molecular and Biochemical Parasitology 84 (1997) 69–82 reported the sub-cellular location of EhCaBP and its functional differences with CaM (Calmodulin).

OBJECTIVES

The main objective of the invention is to modify the homologue(s), of the calcium binding protein gene in plants by recombinant DNA technology for enhanced chlorophyll production and retardation of leaf senescence in plants, and enhanced salt tolerance of seedlings.

Another object is to use of anti-sense and sense gene constructs of a calcium binding protein to manipulate expression of the said or similar genes. An object is to provide a method for expression of EhCaBP gene isolated from the protozoan parasite *E. hystotitica* under the control of a constitutive promoter.

Another object is to provide a method of expressing EhCaBP protein in plants using sense constructs of the said gene, under the control of a constitute promoter.

Yet another object is to develop anti-sense RNA constructs of the EhCaBP protein under the control of a constitute promoter for high level expression in different tissues of the plant.

A further object is to develop transgenic plants transformed with the antisense constructs of the EhCaBP gene and the constitutive promoter.

SUMMARY

Accordingly, the invention provides methods for expression of EhCaBP gene isolated from *E. hystolytica*, under the control of a constitutive promoter, in plants. The invention also relates to the development of transgenic plants transformed with the antisense constructs of the EhCaBP gene and the constitutive promoter.

According to the present invention there is provided methods for enhanced chlorophyll production and enhanced salt tolerance of seedlings. Specifically the present invention relates to the use of anti-sense and sense gene constructs of a calcium binding protein to manipulate expression of the said or similar genes.

DETAILED DESCRIPTION

In accordance with the foregoing objects, the invention provides a nucleic acid construct comprising:
 (a) an anti-sense gene of a sense gene encoding *E. histolytica* calcium binding protein or a portion of said anti-sense gene, wherein said sense gene is at least 90% similar to the nucleic sequence of SEQ ID No: 1, and wherein said portion of the anti-sense gene is of a size capable of disrupting translation of said calcium binding protein;
 (b) a constitutive promoter and a nopaline synthase (nos) polyadenylation signal sequence both operatively linked to said gene or portion thereof, wherein said construct is useful for increasing the level of chlorophyll in plants.

In an -embodiment, the promoter is selected from the group of commercially available promoters comprising CaMV 35S, actin and ubiquitin.

In another embodiment, the preferred promoter is CaMV 35S.

In another embodiment, the antisense gene is at least 90% similar to the nucleic acid sequence of SEQ ID NO:1.

Another embodiment provides a transgenic plant containing a nucleic acid sequence of SEQ ID NO:1.

Further, the invention provides a nucleic acid construct comprising.
 (a) a sense gene encoding *E. histolytica* calcium binding or an altered sense gene wherein said gene encodes proteins of a sequence having biological properties identical to the said sense gene;

(b) a constitutive promoter and a nopaline syntheses (nos) polyadenylation signal sequence both operatively linked to said gene or portion thereof, wherein the said construct is useful in developing stress-tolerant seed plant.

In another embodiment, the promoter is selected from the group of commercially available promoters comprising CaMV 35S, actin and ubiquitin.

In embodiment, the preferred promoter is CaMV 35S.

In yet another embodiment, the antisense gene is at least 95% similar to the nucleic acid sequence of SEQ ID NO.1.

The invention also provides transgenic plants containing a nucleic acid sequence of SEQ ID NO.1.

Further, the invention relates to a method for increasing chlorophyll content in plants, said method comprising the steps of:

a) preparing the nucleic acid construct or sequence of SEQ ID NO.1 capable of manipulation of calcium binding protein, and comprising the gene encoding *E. histolytica* calcium binding protein; and b) transforming a plant with the said construct.

In an embodiment is provided a method for increasing salt tolerance of plants, comprising the steps of:

a) preparing the nucleic acid construct or sequence of SEQ ID NO.1. capable of increasing the concentration of *E. histolytica* calcium binding protein, and comprising the gene encoding *E. histolytica* calcium binding protein; and b) transforming a plant with the said construct.

In one embodiment there is provided a method of using anti-sense *E. histolytica* calcium binding protein (EhCaBP) gene.

The anti-sense constructs of the present invention are under the control of a constitutive promoter, such that chlorophyll accumulation is observed throughout the development of the plants.

Thus, according to one embodiment of the present invention there is provided an anti-sense construct comprising an anti-sense RNA sequence for the *E. histolytica* calcium binding protein (EhCaBP) gene and a constitutive promoter.

In yet further embodiment of the present invention there is provided a transgenic plant comprising an anti-sense RNA sequence for the EhCaBP gene and a constitutive promoter.

In another embodiment of the present invention there is provided a method of expressing EhCaBP protein using sense constructs of the said gene.

The sense constructs of the present invention are under the control of CaMV 35S, a constitutive promoter, such that the transgenic plants express protein and become tolerant to low salinity.

Thus, according to one embodiment of the present invention there is provided an antisense construct comprising a sense RNA sequence for the EhCaBP gene and constitutive promoter.

In yet further embodiment of the present invention there is provided a transgenic plant comprising a sense RNA sequence for the EhCaBP gene and a constitutive promoter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features of the invention will become more apparent from the following description in which references is made to the appended drawings wherein:

FIG. 1 is the DNA sequence of the coding strand, the sense strand of EhCaBP, which encodes a calcium binding protein of *Entamoeba histolytica* which corresponds to SEQ ID NO. 1. The corresponding amino acid sequence of the said gene is also shown in the figure in SEQ ID NO. 2.

FIG. 2 is a map of the anti-sense (a; pBI121-Antisense) and sense (b; pBI121-Sense) constructs of present invention.

FIG. 3 shows a comparison between wild plants and sense plants grown under salt stress conditions.

The abbreviation used in this figure are NosP is nopaline synthase promoter, NPT II is neomycine phosphotransferase II, 35S P is CaMV 35S promoter, uidA is GUS gene, NosT is nopaline synthase terminator, ATG is translation initiation codon, LB is left border, RB is right border. The restriction enzyme used are H is Hind III, Sp is Sph I, P is Pst I, B is BamH I, S is Sma I, E is EcoR I, X is Xho I, Sa is Sst I.

FIG. 3 is a photograph of the T-1 generation seedlings of the sense transgenic plants expressing EhCaBP protein in salt containing medium. The different transformed plants with the sense construct expressing the said *E. histolytica* calcium binding protein are 2S, 10S and 44S, where S means sense plant and WT means wild type or control plants. Sodium Chloride (NaCl, common salt)), $H_2O$ is water

DESCRIPTION OF PREFERRED EMBODIMENT

According to the present invention, manipulation of the concentration of EhCaBP or other similar calcium binding proteins may change the physiology of the plants leading to different phenotypic characters. There are a number of calmodulin-like calcium binding proteins, such as TCH, CDPK, calcium binding pollen allergen (Braam et al., 1997, Planta, 203: S35–S41; Harper et al., 1991, Science, 252: 951–954; Valenta et al., 1998, Int. Arch. Allergy Immunol., 117: 160–166) and EhCaBP is one of the members regarding this a reference can be made to (Prasad et al., 1992, Mol. Biochem. Parasitol., 52:137).

Though EhCaBP was originally obtained from the protozoan parasite *Entamoeba histolytica*, it is likely that a functionally similar protein may exist in other organisms including plants. There is enough data available with us that strongly indicate presence of a EhCaBP-like protein in Brassica sp.

The calcium binding proteins have high degree of sequence homology among each other. For example calmodulin from plants and animals show more than 80% identity at amino acid level among each other. Therefore, it is likely that the putative EhCaBP-like plant proteins may also be similar to each other and to EhCaBP (with respect to amino acid sequence).

In one embodiment of the present invention the sense and anti-sense constructs of EhCaBP were used to generate transgenic tobacco plants. According to the present invention, other plants can also be used to generate transgenics.

Anti-sense and Sense Technology

There are a large number of examples which illustrate that gene expression can be inhibited by the expression of anti-sense RNA regarding this references can be made to (Sheehy et al., 1998, Proc. Natl. Acad. Sci. USA, 85: 8805–8809; Hall et al., 1993, Plant J., 3: 121–129; John et al., 1995, Plant J., 7:483–490; Shimada et al., 1993, Theor. Appl. Genet., 86: 665–672; Atanassova et al.,1995, Plant J., 8:465–477; Wan et al., 1998, Plant J., 15: 459–468; Fan et al., 1997, Plant Cell, 9: 2183–2196; Tang et al., 1999, Plant Cell, 11: 179–189). For example, the level of chlorophyll a/b binding protein regulates the level of chlorophyll. The transgenics containing anti-sense constructs of the chlorophyll a/b binding protein under the control of "site"-specific promoters reduce the level of chlorophyll and therefore degreening of specific parts of plants, such as fruits, flowers etc regarding this a reference can be made to (Johnson-Flanagan et al., 1998, U.S. Pat. No. 5,773,692).

The sense gene is the DNA sequence that produces the correct gene product, that is, the protein if appropriate promoter sequences are attached to the 5'-end. The transgenic plants containing the sense constructs of EhCaBP produce EhCaBP proteins in plants. On the other hand the anti-sense gene is produced when a sense gene is inverted with respect to the promoters and the corresponding constructs are prepared by inverting the coding region of the sense gene relative to its normal presentation for transcription to allow the transcription of the complement. Since anti-sense and sense genes are complementary the former can interfere with the expression of the sense gene. The anti-sense construct can in principle need not be equivalent to full length gene and portion may be sufficient to act as anti-sense and interfere with expression.

According to the present invention EhCaBP gene is cloned in the pBI121 vector which is known in the art, and which is used for the *Agrobacterium tumefaciens* mediated transformation of plants. This pBI121 vector has constitutive promoter, cauliflower mosaic virus 35S promoter (CaMV 35S) and a reporter gene GUS (β-glucurodinase), kanamycin (nptII, neomycin phosphotransferase II gene) for selection of transgenic plant. This said calcium binding gene is cloned in antisense orientation with respect to the CaMV 35S promoter. It was cloned before GUS gene in such a way that the translation initiation codon (ATG) of GUS remained unaltered.

One embodiment of the present invention is related to the expression of EhCaBP gene which has been isolated from the protozoan parasite *E. histolytica*. This gene has been expressed under the control of CaMV 35S promoter. In principle any constitutive promoter could replace CaMV 35S promoter. The examples of such promoters are actin and ubiquitin.

Sense and Anti-sense Constructs

The sense and antisense constructs (or vectors) of the present invention contain the nucleotide sequence coding for EhCaBP and the inverted sequence thereof, respectively. The constructs further contain a constitutive promoter as described above. Other sequence elements, such as, ribosome binding sites, polyadenylation signals, transcription termination sequences, upstream regulatory domains, enhancers and similar well known control elements can be included in the construct. The anti-sense construct may utilize different functional portion of the EhCaBP.

The construct has also a DNA sequence encoding kanamycin, that is used as a marker gene for identification of cells or tissues which have recombinant constructs. Many such selectable markers are known in the art, gentamycin, kanamycin, hygromycin, methotrexate, chlorsulfuron and bleomycin.

Transgenic Plants

Plants transformation can be done according to that described by Horsch et al., 1985, Science, 227: 1229–1231. The Agrobacterium containing sense and antisense constructs of the said *E. histolytica* calcium binding protein gene infect plant cells and the T-DNA (transfer DNA) cassette which contain the said gene get integrated into the plant genome. The said calcium binding gene either in sense in case of sense construct and in antisense in case in case of antisense construct start expressing.

While this invention is described in detail with particular reference to preferred embodiments thereof, said embodiments are offered to illustrate but not limit the invention.

EXAMPLES

Example 1

Construction of a Vector Vontaining Anti-sense EhCaBP

Isolation of pET3c.CaBP Plasmid DNA

This said calcium binding gene is cloned in the vector pET3c and the plasmid containing this said gene is called pET3c.CaBP. For obtaining pure plasmid DNA free of contaminating RNA species, polyethylene glycol purification method was followed. The bacterial culture (30 ml) containing said plasmid clone was harvested and the cell pellet processed with 1 ml, 2 ml and 1.5 ml of solution I (25 mM tris (hydroxymethylaminomethane), pH 8.0, 10 mM ethylenediaminetetraacetic acid (EDTA), 50 mM glucose), solution II (0.2 N NaOH, 1% SDS) and solution III (5M potassium acetate) respectively. The mixture was centrifuged for 10 minutes at 10,000×g, 4° C. The supernatant was treated with 20 μg/ml DNAase (deoxyribonuclease) free RNAase (ribonuclease) and incubated at 37° C. for 30 min. The DNA was extracted with phenol:chloroform:isoamyalcohol (24:24:1) till no precipitate appeared at the interface. It was then precipitated with 0.6 volume of isopropanol for 10 minutes at room temperature. The DNA pellet was resuspended in TE buffer (pH 8.0). To this an equal volume of 1.16 M NaCl containing 13% (W/V) polyethyleneglycol (PEG) was added and the mixture was incubated on ice for 1 hour. DNA was recovered by centrifuging for 15 minutes at 14,000×g. The pellet was washed thrice with cold 70% ethanol and resuspended in TE buffer (pH 8.0). The concentration of DNA was determined by using absorbance at 260 nm (1 OD=50 μg/ml).

Digestion of Plasmid

20 μg of the plasmid DNA was added to the 100 μl of the reaction mixture containing 10 μl of the buffer no. 4 from New England Biolab (50 mM pottassium acetate, 20 mM tris-acetate, 10 mM magnesium acetate, 1 mM dithiothreitol pH 7.9) which contain 70 μl of the sterile water. This reaction mixture was briefly vortexed and centrifuged quickly for very a short time. Then restriction enzymes BamHI and NdeI (5 Units/μg of DNA) were added. Incubated this at 37° C. for 2 h. Use 10 μl of this reaction mixture to check for the digestion on agarose gel electrophoresis.

End Filling Reaction

The digested fragment of the said calcium binding gene was end-filled by adding 1 mM dATP, dTTP, dCTP, dGTP and 1 Unit/μl of Klenow (DNA polymearse) into the reaction mixture. The reaction mixture was incubated for 20 min. at 25° C. (room temperature) and Klenow enzyme was inactivated by heating to 75–85 ° C.

Purification of the End Filled Said Gene Fragment

Cast a 0.8% Agarose gel in 0.5×TBE 45 mM Tris -Borate, 1 mM EDTA. Loaded this end filled reaction mixture to agarose gel and let it separate under the influence of electric current. After staining with ethidium bromide and illuminated under UV-light the end filled said calcium binding gene band was visualized. This band was cut and the DNA fragment was extracted by phenol and finally precipitated by ethanol and sodium acetate. The precipitate was air-dried and dissolved in sterile water.

Isolation of pBI121 and its Restriction Digestion

This plasmid pBI121 is a low copy plasmid that is why it was amplified in the presence of 180 μg/ml chloroamphenicol and then the plasmid was isolated as mentioned in step number 1. This plasmid was added to the reaction mixture containing SmaI buffer and SmaI enzyme. After a brief spin, the reaction mixture was incubated at 25 ° C. for 2 h. After this, part of the reaction mixture was run on gel and checked for the complete digestion.

Joining of the Said Calcium Binding Protein and SmaI pBI121 Vector

This type of joining (ligation) is called blunt end ligation. For blunt end ligation defined amount i.e. 3:1 molar ratio of insert (end filled said calcium binding gene) to SmaI digested vector was taken and added to the reaction mixture containing the T4 DNA ligase buffer, ATP the T4 DNA ligase (0.5 Weiss Units/ml) and 15% PEG 8000 (polyethylene glycol) which stimulates the blunt end ligation. The reaction was carried out at 15° C. for 16–18 h. After the ligation reaction, Sma I (5 units) was added to the reaction mixture in order to decrease the background colonies after transformation of DH5α competent cells.

Isolation of Recombinant Clone

Introduction of the ligated reaction mixture into *E.coli* DH5α competent cells by mixing the recombinant plasmid and competent cells which were prepared by $CaCl_2$ Introduction of this plasmid into *E.coli* cells by conventional heat shock method at 42° C. for 90 second and then addition of LB (Luria Broth Medium) and grown at 37° C. for 1 hour. Then an aliquot was plated on LB-agar plate containing 100 μg/ml kanamycin, and it was incubated at 37° C. overnight.

The recombinant colonies were identified by colony hybridization by radioactive method. In this method, first colonies from the plates were transferred to Nylon membrane, were denatured and renatured. The said calcium binding gene probe was made by Nick translation (Gibco-BRL Kit) as instructed by the manufacturer of the Kit, other kits or reagents can be used for this purpose. A specific activity of $5 \times 10^6$ (counts per min.) cpm/ml was used for hybridization. The prehybridization of nylon filters was done in 6×SSC, 5×Denhardt's (1×Denhardt's reagent is 0.02% each Ficoll, Polyvinylpyrollidone and Bovine Serum Albumin) solution, 20mM $NaH_2PO_4$, pH7.5, 0.5%SDS, 10% Dextran Sulphate and 100 μg/ml denatured salmon sperm DNA for 6–8 hour at 65° C.

Washing of filter was done by SSC, 0.1% SDS wash for 30 min at 65° C.; 0.5×SSC, 0.1% SDS wash for 30min at 65° C. and finally 0.1×SSC, 0.1% SDS wash for 30 min at 65° C. The blots were exposed to X-ray filter and kept at −70° C. for two days. After developing the film, positive colonies were matched to original master plate and picked up. Plasmids from all recombinants were isolated and restriction analysis was done to confirm the antisense recombinant respect to CaMV35.

The second confirmation of antisense orientation was done by sequencing the partial length of DNA from GUS gene (by GUS internal reverse primer). Sequencing was done by sequencing kit (Amersham), by $^{35}S$ radioactive method as per the manufacturer's instructions (it can be done by other kits and reagents). 6% urea polyacrylamide gel was run, dried and exposed to X-ray film at room temperature. After developing the film, nucleotide sequence was read.

Example 2

Sense and Anti-sense Constructs

The pBI121-sense construct was made by inserting NdeI site end filled and intact BamHI site of EhCaBP in the pBI121 vector (Clontech GmbH) under the control of CaMV 35S promoter in such a way that the start (ATG) and stop codon of EhCaBP as well as GUS (uidA) were unperturbed. In this construct both EhCaBP and uidA genes were under the control of CaMV 35S promoter. In antisense constructs of EhCaBP (pBI121-Antisense), the EhCaBP cDNA was end filled at both ends and then inserted into pBI121 vector by blunt end ligation in opposite orientation with respect to CaMW 35S promoter. Here also ATG of uidA (GUS) was undisturbed.

Example 3

Transgenic Plants

Transformation of *Agrobacterium tumefaciens*

Grow the *Agrobacterium tumefaciens* strain LBA 4404 in YEM (Yeast extract 0.04%, Mannitol 1%, NaCl 0.01%, $MgSO_4.7H_2O$ 0.02%, $K_2HPO_4$ 0.05%) at 28° C. o/n in a flask. The culture was grown till the $OD_{600}$ reached 0.5 to 1.0; chill the cells and spin down at 3000×g for 5 min at 4° C. Discard supernatant and resuspend in 20 mM $CaCl_2$. Add 1 ug of the antisense recombinant pBI121 plasmid of the said calcium binding gene and freeze the cells in liquid nitrogen and immediately thaw them by incubating the cells in a 37° C. water bath for 5 min. Add YEM and grow the cells at 28° C. for 4 hours. Spread the cells on a YEM agar plate containing 12.5 μg/ml Rifampicin and 100 μg/ml kanamycin. Incubate the plate at 28° C. for 2–3 days. Confirm the positives recombinant Agrobacterium by colony PCR. In this method, colonies were picked up and mix with 10 μl sterile water, boil it for 5 min and spin down to settle the pellet. The plasmid from the Agrobacterium cell comes into solution after heat lysis. The reaction conditions for PCR were as follow: 5 μg of template DNA, 5 μl of 10×Taq DNA polymerase buffer containing 1 mM $MgCl_2$, 200 μM dNTPs, 1 μM of both forward and reverse primers of calcium binding protein and 5 unit of Taq DNA polymerase enzyme. The thermal cycle conditions were 90 ° C. for 1 min., 50 ° C. for 30 seconds and 72 ° C. for 30 seconds. Total number of cycles used was 30. After PCR of the recombinant clone, agarose gel was run to analyze the PCR product. Those colonies, which showed the presence of strong intense band at 402 bp, were picked up and grown further.

Transformation of Tobacco With Recombinant *Agrobacterium tumefaciens*

Seeds of *Nicotiana tabaccum* var. Xanthi were sterilized and plated on MS-Basal (Murashige and Skoog) media (MS-Major salt, MS-Minor Salt, Fe-EDTA, Sucrose, MS-Vitamin, 0.9% agar).

From 7–8 week old grown plants use the leaf to make the leaf disc by cork borer or paper punch (every thing must be sterilized) and all the steps are to be carried in a sterile laminar flow hood. Dilute the recombinant Agrobacterium over night grown culture to the optical density of 0.6 to 1.0, by MS liquid medium and incubate the leaf disc in this sol for 20 min. Blot dry the excess solution on sterilized filter paper and place them on MS-agar containing 1 µg/ml BAP and 0.1 µg/ml NAA. After 48 hour of co-cultivation, transfer the leaf disc to regeneration media, which is MS-Basal medium containing 1 µg/ml BAP, 0.1 µg/ml NAA and 200 µg/ml kanamycin and 500 µg/ml carbenicellin (selection media). After 15 days, regeneration starts and then transferred the regenerating shoots to MS-rooting media, which is like MS-regeneration media except BAP and IAA (Phytohormone). In two weeks the plantlets started rooting and then were transferred to hardening media and finally transferred to soil.

Antisense Transgenic Plants

Plants were independently transformed with the pBI121-antisense construct (FIG. 2a). Plants (T1 generation) were grown under standard growth conditions and chlorophyll contents of the leaves were determined as described by Arnon (1949, Plant Physiol., 24:1–15). The results are shown below in the Table 1. The EhCaBP antisense plants showed significant increase of chlorophyll when compared to wild type plants.

TABLE NO. 1

Increase in chlorophyll levels in EhCaBP antisense transgenic plants when compared to the wild type plants

| Increase | Chlorophyll a | Chlorophyll b | Total Chlorophyll |
|---|---|---|---|
| mg/g fresh | 0.982 ± 0.1 | 0.63 ± 0.075 | 1.578 ± 0.4 |
| % | 62% | 48.8% | 59.1% |

TABLE NO. 1-continued

Increase in chlorophyll levels in EhCaBP antisense transgenic plants when compared to the wild type plants

| Increase | Chlorophyll a | Chlorophyll b | Total Chlorophyll |
|---|---|---|---|
| | Wild, n = 5 Antisense, n = 5 | | |

Example 4

Sense Transgenic Plants

The levels of chlorophyll did not change in EhCaBP sense plants and they were similar to wild type plants. However the EhCaBP sense transgenic plants showed tolerance to salt stress. T-1 generation seeds were germinated on MS-Basal medium containing 300 µg/ml of kanamycin. After three weeks of growth, the kanamycin positive plants were transferred to MS-Basal media containing different concentration of salt. The plants were grown at 25±2° C. for 16 hours of soft fluorescent light and 8 hours of darkness for 4 weeks (standard tissue culture condition).

Figure 3:
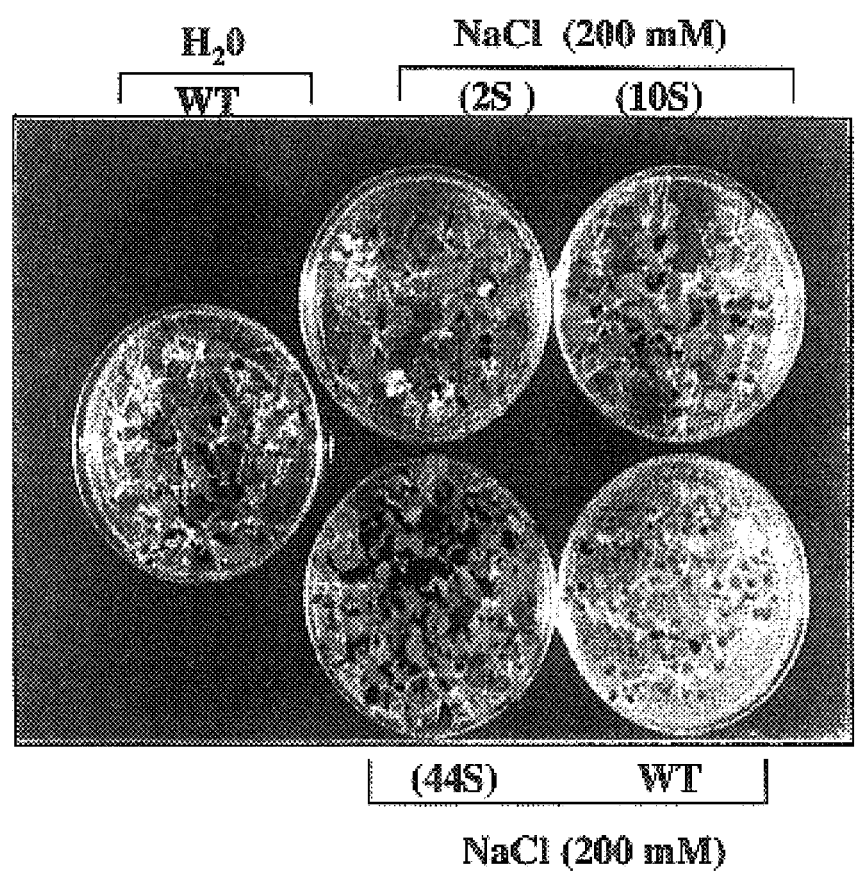

The seeds raised from sense plants were tested for their growth under salt stress conditions. Compared to wild type seeds, the seeds of sense plants were able to grow even under salt (200 mM NaCl) condition as shown in the FIG. 3. This is evident from the FIG. 3 is that the EhCaBP sense transgenic plant could grow much better in comparison to wild type seedling which showed retarded growth at 200 mM NaCl. Thus from FIG. 3, it is clear that the sense plants showed tolerance to salt stress as the seeds of T1 generation were able to grow under exogenous presence of 200 mM salt (NaCl).

SEQUENCE LISTING

<160> NUMBER OF SEQ ID NOS: 2

<210> SEQ ID NO 1
<211> LENGTH: 405
<212> TYPE: DNA
<213> ORGANISM: Entamoeba histolytica
<220> FEATURE:
<221> NAME/KEY: CDS
<222> LOCATION: (1)..(405)

<400> SEQUENCE: 1

```
atg gct gaa gca ctt ttt aaa gaa att gat gtt aat gga gat gga gct      48
Met Ala Glu Ala Leu Phe Lys Glu Ile Asp Val Asn Gly Asp Gly Ala
1               5                   10                  15 gtc tct tat gaa gaa gtt aaa gct ttt gtt tca aag aag aga gca att      96
Val Ser Tyr Glu Glu Val Lys Ala Phe Val Ser Lys Lys Arg Ala Ile
                20                  25                  30 aag aat gaa caa ctt ctt caa tta att ttc aaa tct att gat gct gat     144
Lys Asn Glu Gln Leu Leu Gln Leu Ile Phe Lys Ser Ile Asp Ala Asp
            35                  40                  45 gga aat gga gaa aat gat caa aat gaa ttt gct aaa ttc tat gga tca     192
```

-continued

```
Gly Asn Gly Glu Asn Asp Gln Asn Glu Phe Ala Lys Phe Tyr Gly Ser
    50                  55                  60 att caa gga caa gat ctt tct gat gat aag att gaa ttg aaa gta ctc    240
Ile Gln Gly Gln Asp Leu Ser Asp Asp Lys Ile Glu Leu Lys Val Leu
65                  70                  75                  80 tat aaa ctt atg gat gtt gat gga gat gga aaa tta act aaa gaa gaa    288
Tyr Lys Leu Met Asp Val Asp Gly Asp Gly Lys Leu Thr Lys Glu Glu
                85                  90                  95 gtt act tca ttc ttt aaa aag cat ggt att gaa aag gtt gct gaa caa    336
Val Thr Ser Phe Phe Lys Lys His Gly Ile Glu Lys Val Ala Glu Gln
            100                 105                 110 gtt atg aaa gct gat gct aat ggt gat gga tat atc aca ctt gaa gaa    384
Val Met Lys Ala Asp Ala Asn Gly Asp Gly Tyr Ile Thr Leu Glu Glu
        115                 120                 125 ttc ctt gag ttt tca ctc taa                                        405
Phe Leu Glu Phe Ser Leu
    130
```

<210> SEQ ID NO 2
<211> LENGTH: 134
<212> TYPE: PRT
<213> ORGANISM: Entamoeba histolytica

<400> SEQUENCE: 2

```
Met Ala Glu Ala Leu Phe Lys Glu Ile Asp Val Asn Gly Asp Gly Ala
1               5                   10                  15

Val Ser Tyr Glu Glu Val Lys Ala Phe Val Ser Lys Lys Arg Ala Ile
                20                  25                  30

Lys Asn Glu Gln Leu Leu Gln Leu Ile Phe Lys Ser Ile Asp Ala Asp
            35                  40                  45

Gly Asn Gly Glu Asn Asp Gln Asn Glu Phe Ala Lys Phe Tyr Gly Ser
    50                  55                  60

Ile Gln Gly Gln Asp Leu Ser Asp Asp Lys Ile Glu Leu Lys Val Leu
65                  70                  75                  80

Tyr Lys Leu Met Asp Val Asp Gly Asp Gly Lys Leu Thr Lys Glu Glu
                85                  90                  95

Val Thr Ser Phe Phe Lys Lys His Gly Ile Glu Lys Val Ala Glu Gln
            100                 105                 110

Val Met Lys Ala Asp Ala Asn Gly Asp Gly Tyr Ile Thr Leu Glu Glu
        115                 120                 125

Phe Leu Glu Phe Ser Leu
    130
```

What is claimed is:

1. A nucleic acid construct comprising:
   (a) the full length anti-sense gene of the sense gene of SEQ ID NO:1 encoding an *E. histolytica* calcium binding protein; wherein said anti-sense gene is capable of disrupting translation of said calcium binding protein; and
   (b) a constitutive promoter and a nopaline synthase (nos) polyadenylation signal sequence both operatively linked to said anti-sense gene; wherein said construct is useful for increasing the level of chlorophyll.

2. The construct as claimed in claim 1 wherein the promoter is selected from the group consisting of CaMV 35S, actin and ubiquitin.

3. A The construct as claimed in claim 1 wherein the promoter is CaMV 35S.

4. A transgenic plant containing the nucleic acid construct as claimed in claim 1.

5. A method for increasing chlorophyll content in plants, said method comprising the steps of:
   a) preparing the nucleic acid construct of claim 1 capable of decreasing the concentration of the *E. histolytica* calcium binding protein; and
   b) transforming a plant with the said construct.

* * * * *